(12) United States Patent
Zhu et al.

(10) Patent No.: US 6,610,907 B1
(45) Date of Patent: Aug. 26, 2003

(54) COTTON LEAF CURL VIRUS (CLCUV) PROMOTER AND ITS USE

(75) Inventors: Zhen Zhu, Beijing (CN); Yingqiu Xie, Beijing (CN); Yule Liu, Beijing (CN)

(73) Assignee: Institute of Genetics Chinese Academy of Science, Beijing (CN)

( * ) Notice: Subject to any disclaimer, the term of this patent is extended or adjusted under 35 U.S.C. 154(b) by 0 days.

(21) Appl. No.: 09/936,552

(22) PCT Filed: Feb. 18, 2000

(86) PCT No.: PCT/CN00/00030

§ 371 (c)(1),
(2), (4) Date: Sep. 14, 2001

(87) PCT Pub. No.: WO00/56895

PCT Pub. Date: Sep. 28, 2000

(30) Foreign Application Priority Data

Mar. 22, 1999 (CN) .......................................... 99 1 03044

(51) Int. Cl.[7] .................. C12N 15/82; C12N 15/90; C12N 5/04; A01H 5/00; C07H 21/04
(52) U.S. Cl. ........................ 800/278; 435/468; 536/24.1
(58) Field of Search ............................. 435/69.1, 320.1, 435/419, 468; 536/24.1; 800/278, 288, 298, 295

(56) References Cited

PUBLICATIONS

Sanz et al., J. Mol. Evol., 1999, vol. 49, pp. 672–681.*
Zhou et al., J. Gen. Virol., 1998, vol. 79, pp. 915–923.*
Benfey et al, "The Cauliflower Mosaic Virus 35S Promoter: Combinatorial Regulation of Transcription in Plants", Nov. 1990, Science vol. 250, pp. 959–966.*
Kim et al, "A 20 nucleotide upstream element is essential for the nopaline synthase (nos) promoter activity", 1994, Plant Molecular Biology vol. 24, pp. 105–117.*
Freeman et al, "Quantitative RT–PCR: Pitfalls and Potential", BioTechniques vol. 26 No. 1, pp. 112–125.*
Promega Protocols and Applications Guide, 1996, pp. 198–200.*

* cited by examiner

*Primary Examiner*—Ashwin Mehta
(74) *Attorney, Agent, or Firm*—Morgan & Finnegan, LLP

(57) ABSTRACT

The present invention is directed to a cotton leaf curl virus (CLCUV) bi-directional promoter, a method of expressing a heterologous gene in various plant tissues at a high level using the cotton leaf curl virus bi-directional promoter, and an AC2 protein factor from CLCuV genome to improve the expression level of the coat protein-coding gene promoter in the bi-directional promoter. The expression of a heterologous gene in plants is improved by using the materials and methods of the present invention.

9 Claims, 9 Drawing Sheets

Figure 3:
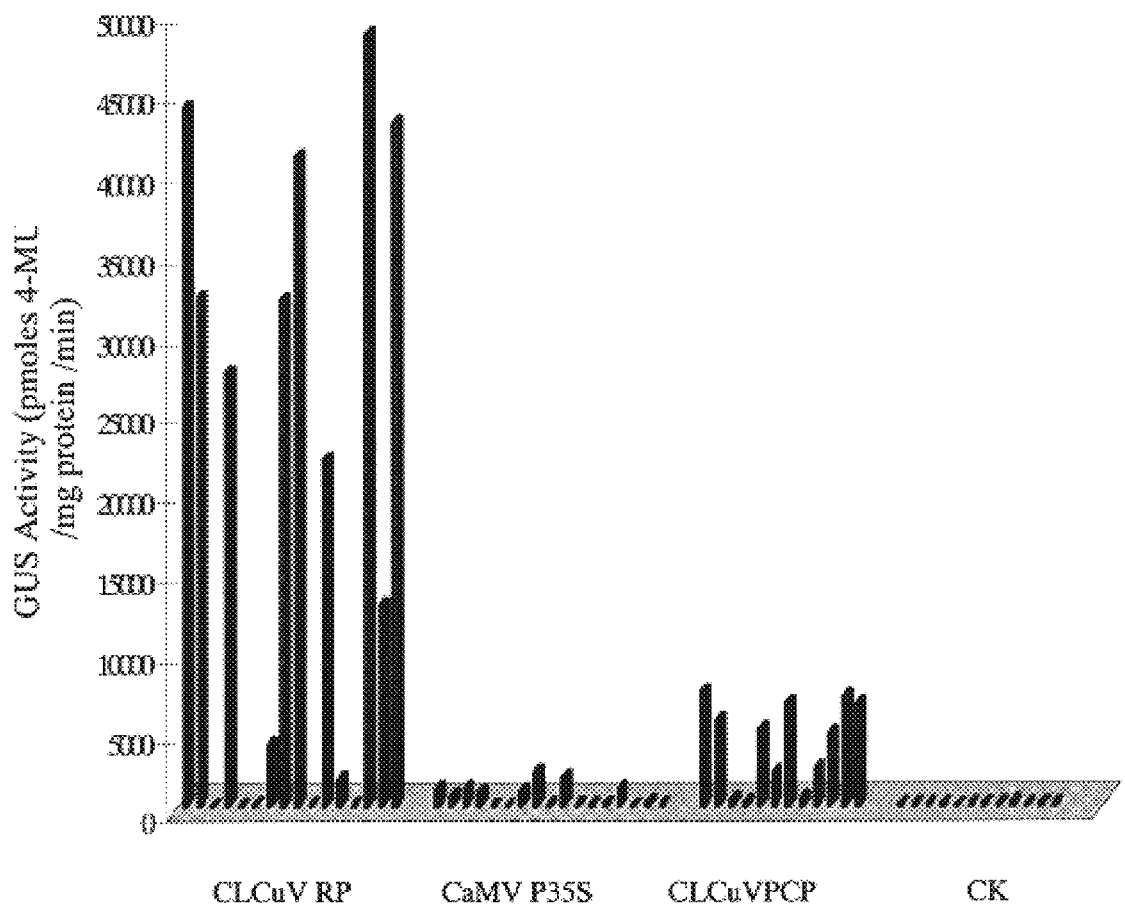

```
  1 GGTACCATGG  TGGCAATCGG  TGTACACTCT  AATTCTCTGG    40
2581                                                2620
 41 CAATCGGTGT  AACGGGGTGC  AATATATAGG  TGTACCCCAA    80
2621                                                2660
 81 ATGGCATTAT  CGTAATTTGA  GAAATCATTT  CAAAATCCTC   120
2661                                                2700
121 ACGCTCCAAA  AAGCGGCCAT  CCGTATAATA  TTACCGGATG   160
701                                 ←   E         15
161 GCCGCGCTTT  TTTTTTTGTG  GGCCCCCGAT  TTACGAGATT   200
 16                     ←   B                     55
201 GCTCCCTCAA  AGCTAAATAA  CGCTCCCGCA  CACTATAAGT   240
 56                                                  5
241 ACTTGCGCAC  TAAGTTTCAA  ATTCAAACAT  GTGGGATCCA   280
 96                                     C  ← 135
281 CTATTAAACG  AATTCCCTGA  TACGGTTCAC  GGGTTTCGGT   320
136         ←   D                                  175
321 GTATGCTTTC  TGTGAAATAT  TTGCAACTTT  TGTCGCAGGA   360
176                                                215
361 TTATTCACCG  GATACGCTTG  GGTACGAGTT  AATACGGGAT   400
216                                                255
401 TTAATTTGTA  TTTTACGCTC  CCGTAATCAT  GAGCTC       436
256                                     ←  A    292
```

SEQ ID NO:1

Figure 1

```
  1      c gcg aat tcc tag acg agg aaa aga aca ccg cac          34

35      taa aga act ggg cag taa aga ATG CGA TCT TCA TCA         70
                                     Met Arg Ser Ser Ser    5

71      CAC TTG ATA GAC CCC TGT ACT CAG GTA CCA ATC AAA        106
  6      His Leu Ile Asp Pro Cys Thr Gln Val Pro Ile Lys         17

107      GTA CAG CAC AGG GAA GCG AAG AGG CGC AAC AGG AGG        142
 18      Val Gln His Arg Glu Ala Lys Arg Arg Asn Arg Arg         29

143      AGG AGA GTA GAT CTT GAA TGC GGG TGT TCT TAT TAT        178
 30      Arg Arg Val Asp Leu Glu Cys Gly Cys Ser Tyr Tyr         41

179      CTG TCA ATC AAC TGC CAC AAC CAT GGA TTC ACG CAC        214
 42      Leu Ser Ile Asn Cys His Asn His Gly Phe Thr His         53

215      AGG GGA ACC CAT CAC TGC AGC TCA AGC AGG GAA TGG        250
 54      Arg Gly Thr His His Cys Ser Ser Ser Arg Glu Trp         65

251      CGC ATA TAT CTG GGA GGT TCC AAA TCC CCT TTA TTT        286
 66      Arg Ile Tyr Leu Gly Gly ser Lys Ser Pro Leu Phe         77

287      CAA GAT CAT CAG CCA CGT CAA CCG TCC ATT CAC GAC        322
 78      Gln Asp His Gln Pro Arg Gln Pro Ser Ile His Asp         89

323      GAA TAT GGA CAT ACT CAC GAT CAG GAT CCA GTT CAA        358
 90      Glu Tyr Gly His Thr His Asp Gln Asp Pro Val Gln        101

359      CTA CAA CAC TCG GAA AGC TCT GGG ACT GCA CAC GTG        394
102      Leu Gln His Ser Glu Ser Ser Gly Thr Ala His Val        113

395      TTT TCT AAC CTT CCG AAT CTG GAC GAC CTT ACA GCC        430
114      Phe Ser Asn Leu Pro Asn Leu Asp Asp Leu Thr Ala        125

431      TCA GAC TGG TCT TTT CTT AAG GGT ATT CAA AAC CCA        466
126      Ser Asp Trp Ser Phe Leu Lys Gly Ile Gln Asn Pro        137

431      AGT CCT CAA ATA TCT GAA CAA TCT CGG TGT AAT TTC        502
138      Ser Pro Gln Ile Ser Glu Gln Ser Arg Cys Asn Phe        149

503      AAT TAA TAG agt cga ccg g                              521
150      Asn *** ***                                            151
```

Figure 2

Figure 7

COTTON LEAF CURL VIRUS (CLCUV) PROMOTER AND ITS USE

FIELD OF THE INVENTION

The present invention relates to isolated cotton leaf curl virus promoters and method for expressing heterologous genes of interest in plant cells by using the promoter.

BACKGROUND OF THE INVENTION

Plant genetic engineering is aimed to breed transgenic plants that steadily express genes of interest at high level. Gene expression is controlled by the nucleotide sequence within the initiation site of transcription, called promoter elements, and include signals for promotion of transcription by RNA polymerase. Transcription results in the production of messenger RNA, which in turn results in the synthesis of protein.

So far, a variety of promoters derived from various resources have been applied in plant transformation. A main category of which was isolated from Agrobacterium. Another category was derived from plants. The expression levels of genes controlled by these two category of promoters are usually too low or the expression is species/varieties specific, or tissue/organ specific. The most extensively used promoters come from plant viruses. The 35S promoter of cauliflower mosaic virus is one of the most widely used promoters in dicotyledonous plant transformation as it can lead high level expression of heterologous genes in most tissues. Furthermore, in order to enhance the expression of heterologous genes, promoters are usually used in combination with enhancers, cis-elements, non-transcription sequences, intron, exon and 3' control sequences and the like. For example, the expression level of GUS reporter gene could be enhanced up to 100-fold by using the intron 1 of maize shrunken-1 gene in tobacco cells, and could be enhanced up to 10-fold by using the first exon of maize shrunken-1 gene (C. Mass et al., 1991, "The Combination of Novel Stimulatory Element in the First Exon of the Maize Shrunken-1 Gene with the following Intron-1 Enhances Reporter Gene Expression up to 1000-fold", Plant Mol. Biol., 16: 199–207).

Promoters from plant geminiviruses could be potentially used in heterologous gene expression. Geminivirus is a bipartite virus with twin particles. There are numerous members of geminivirus and they infect many crops of different kinds. The geminiviruses are classified into three subgroups based on their genome structure and the insect on which they rely for transmission. In subgroup I and II, the geminivirus genomes are mono partite, namely single genome. These two subgroups of geminiviruses are mainly transmitted by leafhopper. The differences between these two subgroups consist in that the former mainly infects monocotyledonous plants while the latter mainly infects dicotyledonous plants. The subgroup III of geminivirues mainly infect dicotyledonous plants and are transmitted by whitefly. Their genome is mostly bipartite, in which the larger one is called DNA A and the smaller one is called DNA B. The genome of some of the subgroup is mono partite.

A prominent characteristic of geminiviruses is that the genomic DNA is circular and single stranded, with a length of about 2400–3000 nucleotides. Another prominent characteristic of geminivirus genome is the bidirectional transcription controlled by the same promoter. The promoter can initiate transcription in two directions, therefore, the promoter is called a bidirectional promoter. One of the two directions controlsexpression of the viral replication protein gene, the other controls the expression of the coat protein gene. Thus, the two directions of the promoter are named the replication protein gene promoter and the coat protein gene promoter, respectively. The geminivirus promoter shares some features of a typical eukaryotic promoter which comprises a TATA box upstream of transcription initiation sites (P. A. Eagle et al., 1997, "Cis-Elements Tthat Contribute to Geminivirus Transcriptional Regulation and the Efficiency of DNA Replication", J. Virol., 71: 6947–6955).

X. Zhan et al. (X. Zhan et al., 1991, "Analysis of the Potential Promoter Sequence of African Cassava Mosaic Virus by Transient Expression of the β-Glucuronidase Gene", J. Gen. Virol., 72: 2849–2852) isolated a bidirectional promoter from African cassava mosaic virus(ACMV) genome which belongs to subgroup III. Transient expression in tobacco protoplast showed that GUS reporter gene expression activity controlled by replication protein gene promoter was 40-fold lower than that of CaMV 35S promoter. The activity of the coat protein gene promoter was very low when used alone. However, the activity can be increased up to 3-fold by the ACMV coded AC2 protein under the control of CaMV 35S promoter (Haley, A. et al., 1992, "Regulation of African Cassava Mosaic Virus Promoters by the AC1, AC2, AC3 Gene Products", Virology, 188: 905–909).

By transforming a plant using TGMV introduced into Agrobacterium as a gene vector, R. J. Hayes et al. found that the reporter gene activity of neomycin phosphotransferase (NPTII) controlled by coat protein gene promoter from tomato golden mosaic virus(TGMV) activated by AC2 was not as strong as the CaMV 35S promoter, and was 2-fold lower than that of CaMV 35S promoter. (R. J. Hayes et al., 1989, "Replication of Tomato Golden Mosaic Virus DNA B in Transgenic Plants Expressing Open Reading Frames (ORFs) of DNA A: Requirement of ORF AL2 for Production of Single-Stranded DNA", Nucl. Acids Res., 17: 10213–10222).

C. Brough et al. (C. Brough et al., 1992, "Kinetics of Tomato Golden Mosaic Virus DNA Replication and Coat Protein Promoter Activity in Nicotiana Tabacum Protoplast", Virology, 187: 1–9) found that transient expression activity of GUS gene controlled by the coat protein gene promoter was up to 2-fold higher than that by the CaMV 35S promoter, which was demonstrated by using non-replicative TGMV vectors for plant transformation. However, the activity of replicative TGMV coat protein gene promoter was about 60–90-fold of that of CaMV 35S promoter.

Xu Yuquan et al. (Y. Xu et al., 1998, "Activity and Transcriptional Regulation of Bidirectional Promoter from Tobacco Yellow Dwarf Geminivirus", Chinese Journal of Virology, 14: 68–74) isolated a subgroup III bidirectional promoter from tobacco yellow dwarf geminivirus, and found that the replication protein gene promoter was stronger and has an activity of 15–20% of the CaMV 35S promoter as demonstrated by transient expression of GUS as a reporter gene in tobacco protoplast and maize cell suspension. The activity of the coat protein gene promoter was weaker but could be increased by C1: C2 protein(corresponding to AC2 protein) by 3-fold.

Most of the previous studies on bidirectional promoters have been carried out by using transient expression. X. Zhan et al. (X. Zhan et al., 1991, "Analysis of the Potential Promoter Sequence of African Cassava Mosaic Virus by Transient Expression of the β-Glucuronidase Gene", J. Gen. Virol., 72: 2849–2852) found that the activity of ACMV replication protein gene promoter was lower than that of the CaMV 35S promoter as demonstrated by Agrobacterium mediated transformation. Briefly, the activities of the presently isolated geminivirus promoters are lower than that of the CaMV 35S promoter. According to this invention, a promoter was isolated from cotton leaf curl virus which belongs to subgroup III of geminivirus and the activity of the promoter was studied by using GUS as the reporter gene.

Cotton Leaf curl virus (CLCuV) is a geminivirus that was found to have infested various crops in Pakistan, Sudan, and India in recent years. According to the statistics for 1993–1994 published by the Pakistan Government, the area of cotton field infested by CLCuV was up to 900,000 hectares and the loss of yield was about 80% (M. Ali et al., 1995, "Cotton Leaf Curl Virus in the Punjab: Current Situation and Review of Work", Multan: Central Cotton Research Institute/Ministry of food, Agriculture and Livestock, Government of Pakistan/Asian Development Bank). It has been demonstrated that CLCuV was transmitted by whitefly. The virus affects a wide spectrum of crops, including French bean, okra, tobacco, tomato, cotton and the like. The affected plants show thick leaf veins and yellowish leaves. At present, at least nine varieties of CLCuV have been found. X. Zhou et al. (X. Zhou et al., 1998, Four DNA-A variants among Pakistani isolates of cotton leaf curl virus and their affinities to DNA-A of geminivirus isolates from okra. J. Gen. Virol., 79: 915~923) studied the evolution of CLCuV based on the DNA sequences of different varieties. Until now no report has been seen on the application of CLCuV bidirectional promoter in plant genetic engineering.

Great progress has been achieved by way of plant genetic engineering in the field of disease-resistant, insect-resistant, herbicide-resistant, stress-resistant, improvement of crop quality, enhancement of the ability of nitrogen fixation, male sterility, delaying maturity and maintaining freshness, changing the flower colors and shapes. However, the expression levels of genes are still low and unstable, hindering the development of plant genetic engineering. Furthermore, most of the presently used promoters are species or variety-specific, organ or tissue-specific. There still exits a need to develop stronger promoters which can be used in heterologous gene expression in plants.

DISCLOSURE OF THE INVENTION

It is an object of the present invention to provide a stronger promoter suitable for transformation of monocotyledonous plants and dicotyledonous plants which can be used for constitutive expression of genes of interest in plants.

The present invention provides a bidirectional promoter derived from a plant virus.

The bidirectional promoter of the present invention constitute a part of the geminivirus genome, the large intergenic region (LIR) in the genome. The LIR comprises a promoter region and regulatory elements for bidirectional transcription, which plays an important role in the replication and bidirectional transcription of the virus.

Specifically, the promoter of the present invention is a part of the cotton leaf curl virus genome. More specifically, the promoter of the present invention has the sequence, SEQ ID NO: 1, shown in FIG. 1.

Preferably, the promoter of the present invention is the full-length promoter element with nucleotides 1–436 of the sequence shown in SEQ ID NO: 1. This promoter can lead to high level expression of heterologous genes in, for example but not limited to, plants and Agrobacterium tumifaciens. This promoter can also be used in combination with the promoters from other sources in the expression of heterologous genes.

The promoter of the present invention can be truncated, nucletides 1–184 of SEQ ID NO: 1. The truncated promoter can lead to high level expression of a heterologous gene in roots as well as in other organs such as stems and leaves of plants. The truncated promoter may also be used in combination with the promoters from other sources in the expression of heterologous genes.

The promoter of the present invention may be a second truncated form, nucleotides 1–278 of SEQ ID NO:1. This second truncated promoter can lead to high level expression of a heterologous gene in, for example, but not limited to, plants and Agrobacterium tumifaciens. This second truncated promoter may also be used in combination with the promoters from other sources in the expression of a heterologous gene.

The promoter of the present invention may further be in a third truncated form, with nucleotides 1–294 of SEQ ID NO:1. This third truncated promoter can lead to a high level expression of a heterologous gene in, for example, but not limited to, plants and Agrobacterium tumifaciens. This third truncated promoter may also be used in combination with the promoters from other sources in the expression of heterologous genes.

The bidirectional promoter of the present invention is derived from the LIR region of the CLCuV genome. The promoter can be isolated from the native CLCuV genome or synthesized by using PCR or any conventional chemical synthesis method. CLCuV belongs to subgroup III and includes a number varieties. At present, nine different strains have been found in Pakistan. In a preferred embodiment of the present invention, the bi-directional promoter is isolated from a new CLCuV strain, and has the sequence illustrated in FIG. 1.

The promoters provided by this invention can be used in either one direction for controlling heterologous gene expression or in both directions at the same time. The promoter may also be used as a combination promoter by linking its controlling elements with other promoter elements. Those skilled in the art will appreciate that, mutation (s) or deletion(s) performed on the bidirectional promoter to the nucleotides beyond the TATA box core region do not affect to a significant extent the activity of the promoter under some circumstances. If desired, the regulatory elements of the bidirectional promoter can be modified before they are used. Therefore, promoters which share 80% identity of the promoter shown in FIG. 1 are also encompassed by the present invention.

Preferably, the promoter provided by this invention includes upstream region of transcription initiation site (position +1), and does not include the region between transcription initiation site and translation initiation site (ATG). The transcription initiation site of an eukaryote is characterized by a sequence of YYYAYA (wherein, Y represents pyrimidine), and transcription starts at the $4^{th}$ nucleotide which is A. The transcription initiation site of the replication protein gene promoter is at position 2606 which is A, and the transcription initiation site of the coat protein gene promoter is at position 255 which is T, by homology analysis with other known geminivirus genomes.

It is another object of the present invention to provide a method for heterologous gene expression in plants using the promoter of the present invention. The method includes the following steps:
  (a) Constructing a plant expression vector by linking the cloned bi-directional promoter from CLCuV with a heterologous gene to be expressed,
  (b) Transforming plant cells with the constructed plant expression vector,
  (c) Regenerating the transformed plant cells under appropriate culture conditions into plants and identifying and obtaining the transformed plants expressing the heterologous genes.

The promoter used in the method of the present invention is a bidirectional promoter from cotton leaf curl virus. Specifically, the promoter has a sequence illustrated in FIG. 1 or a truncated promoter as mentioned above. The promoter can be isolated from the virus or synthesized chemically.

The promoter used in this method is called bidirectional promoter because the promoter functions in two directions. The gene to be expressed can be linked with the promoter in two different directions.

Preferably, the promoter provided by this invention includes upstream region of transcription initiation site (position +1), and does not include the region between the transcription initiation site and the translation initiation site (ATG). The transcription initiation site of the eukaryote is characterized by a sequence of YYYAYA (SEQ ID NO:4), wherein, Y represents pyrimidine), and the transcription starts at the $4^{th}$ nucleotide, A. The transcription initiation site of the replication protein gene promoter is at position 2606, A, and transcription initiation site of the coat protein gene promoter is at position 255 T, by homology analysis with other known geminivirus genomes.

Preferably, a promoter useful in this method includes a regulatory element, a cis-element, such as the tissue specific (root-specific, mesophyll-specific, seed endosperm-specific floral organ-specific, fruit-specific, vascular-specific) elements; an inducible element, such as, a wound inducible element; an enhancer element for enhancing heterologous gene expression, or a negative regulatory element for reducing heterologous gene expression as desired. It is known to those skilled in the art that a promoter which lead to constitutive expression is generally composed of a number of modular cis-elements. The presence of regulatory elements determine the characteristics of gene expression, and can be used in combination with a promoter from a different source. The cis-elements of the bidirectional promoter are also included in this invention.

More preferably, the promoter used in this method includes not only the core promoter sequences required for viral gene transcription such as the TATA box, but also includes other cis-elements and elements related to viral replication such as the conserved hairpin and its neighboring sequences, 5'-GCTCCAAAAAGCGGCCATCCGTATAAT ATTACCGGATGCCGCGCTTTTTTTTTTGTG-3' (SEQ ID NO:5). Generally, the activity of the promoter would not totally be lost if the sequences beyond the TATA box core region were modified by mutation or deletion. Therefore, if desired, the regulatory elements of the bi-directional promoter can be modified before it is used. Thus, DNA sequences which have approximately 80%, preferably 99%, nucleotide identity with the sequences shown in FIG. 1 are also included in this invention.

The promoter used in this method can include an additional regulatory element (such as an enhancer element) from the CaMV 35S promoter, ocs promoter (L. Comai et al., 1985, "Expression in Plants of a Mutant AcroA Gene from Salmonella Typhimurium Confers Tolerance to Glyphosate", Nature, 317: 741–744), mas promoter (K. E., McBride et al., 1990, "Improved Binary Vectors for Agrobacterium-Medidated Plant Transformation", Plant Mol.Biol., 14: 269–276) to form a combinatory promoter. Moreover, the bidirectional promoter may be placed upstream of any a translation enhancer element to regulate heterologous gene expression. The translation enhancer elements include a non-translation sequence AMV from Alfafa mosaic virus(AMV) (S. A Jobling et al., 1987, "Enhanced Translation of Chimeric Message RNAs Containing a Plant Viral Untranslated Leader Sequence", Nature, 325: 622–625), Ω factor from tobacco mosaic virus (K. Richards et al., 1978, "Nucleotide Sequence at the 5' Extremity of Tobacco Mosaic Virus RNA", Eur. J. Biochem., 84: 513–519) and the like. In the chimeric gene constructs, DNA sequences which can enhance heterologous gene expression can also be included. The DNA sequences include but are not limited to an intron, such as the rice Actin 1 intron, the maize Ubquin intron 1, the maize S-1 intron of ethanol dehydrogenase gene 1, or an exon such as the maize Sh1 exon 1 of sucrose synthetase gene and 3' regulatory element such as PI-II gene terminator.

The bidirectional promoter in the method of this invention can be linked with a heterologous gene either in the direction of the replication of the protein gene or in the direction of the coat protein gene. The activity of the promoter in the direction of the CLCuV coat protein gene is very low by itself. It can be activated by the AC2 protein encoded by CLCuV genome. Therefore, in the method of this invention, the AC2 protein gene (the DNA sequence is illustrated in FIG. 2) can be co-expressed if the bidirectional promoter were linked with a heterologous gene in the direction of the coat protein gene.

The expression of the AC2 protein gene can be controlled by any of the known promoters, which include, but are not limited to, the CLCuV promoter, the CaMV 35S promoter, the tomato E8 promoter, the Gt3 promoter, rolc promoter, the CoYMV promoter, the rbcs promoter, the hsp70 promoter and the PI-II promoter and the like.

The GUS reporter gene was used in the method of this invention. For the purpose of the present invention, a reporter gene means a nucleic acid sequence fused down stream to the promoter. The promoter can direct transcription of the reporter gene and translation of the reporter gene will produce biochemical substances which can be easily detected by beta-glucuronidase(GUS). In this invention, promoter activity was determined by measuring the activity of beta-glucuronidase in tobacco and cotton cells.

The heterologous gene in this invention can be any of the genes targeted for altering a genetic trait of a plant. These include but not limited to non-coding genes such as RNA genes (include but not limited to sense RNA and anti-sense RNA), and coding genes (include but not limited to genes for insect-resistant, disease-resistant, stress-resistant, herbicide-resistant, improvement of crop quality) which can be used together with the promoter and inserted into vectors and for expression in plant cells.

Gene manupulation can be carried out by know techniques described in, for example, J. Sambrook et al., 1989, "Molecular Cloning, A Laboratory Manual", Cold Spring Harbor Laboratory Press, Cold Spring Harbor, N.Y. Transformation of plants can be performed by the method of, for example, gene gun transformation, leaf-dic *Agrobacterium tumifaciens* transformation, PEG transformation and the like.

The promoter of the present invention can be used in dicotyledonous plants (include but not limited to cotton, tobacco) for expression of a heterologous gene. It can also be used in monocotyledonous plants, but the expression level of genes controlled by dicotyledonous plant promoters in monocotyledonous plants is not as high. Tobacco is a widely used model plant because it can be easily regenerated and the transformation efficiency is high using *Agrobacterium tumifaciens* Ti plasmid vector. Dicotyledonous plants such as cotton, tomato, rape, French bean, okra, tobacco and monocotyledonous plants such as grains, for example rice, wheat, maize, barely, oats are preferred hosts for transformation.

The evaluation of gene expression level controlled by the promoter can be carried out by any of the known method in the art, which include, for example, fluorescence spectrophotometry for analysis of GUS, or a histochemical assay, such as the hand cut method or the frozen cut method.

Another subject of the present invention is the use of the AC2 protein encoded by the CLCuV genome to enhance the gene expression level directed by the coat protein gene promoter.

The AC2 protein gene can be found in the total DNA of CLCuV infected plant tissues. It is derived from CLCuV genome and can be obtained by PCR, extraction or chemical synthesis. The amino acid sequence and the corresponding nucleotide sequence are shown in SEQ ID NO: 2 and the deduced amino acid sequence shown in SEQ ID NO:3 in FIG. 2.

The expression of AC2 can be controlled by any of the known promoters able to function in plant cells to regulate the activity of the coat protein gene promoter. Such promoters include, but not limit to, the CLCuV promoter, the CaMV 35S promoter, the tomato E8 promoter, the Gt3 promoter, the rolc promoter, the CoYMV promoter, the rbcs promoter, the hsp7O promoter, and the PI-II promoter.

The promoter of the present invention functions in two directions. The promoter in one direction, the full length replication protein (RP) gene promoter, can direct heterologous gene expression at a level 5.4 times higher than that of the CaMV 35S promoter on average, with the highest level of expression reaching 10 times that of the CaMV 35S promoter. The full-length promoter in this direction can direct heterologous gene expression efficiently in plant roots, stems, and leaf organs, with the highest level in roots.

TABLE 1

Comparison of GUS expression activity directed by CLCuV replication protein gene promoter in various tissues

| Construct | Leaves | Stems | Roots |
|---|---|---|---|
| CLCuV PRP-GUS | 39,898 ± 6,674 | 27,297 ± 30,009 | 75,224 ± 2,2946 |
| CaMV 35S-GUS | 5,519 ± 1,862 | 2,678 ± 1,170 | 11,788 ± 2,848 |
| Control | 135 ± 42 | 411 ± 162 | 671 ± 974 |

Notes:
the data in the table is an average of 6 assay of transformant seedlings (T0 generation) which steadily expressed GUS gene. The transformants were obtained by transformation mediated by *Agrobacterium tumifaciens*. The data were shown by average ± standard deviation. The unit is pmoles MU/mg protein/min. CLCuV PRP represents the CLCuV replication protein gene promoter, CaMV 35S represents the CaMV 35S promoter.

Histochemical analysis demonstrated that the full length replication protein gene promoter showed activity in mesophyll (including palisade and spongy mesophyll tissues) and vascular tissues. Staining of the stem sections showed that strong GUS staining was detected in both external and internal phloem cells and in the xylem parenchyma cells. In the section prepared from an unfertilized flower, GUS staining was detected in calyx, corolla, ovary, stigma and tapetal. In immature fruits, GUS staining was present on the outside wall. In mature seeds, GUS activity was present in the embryo and the surrounding endosperm tissues.

A heterologous gene can be expressed at a high level in roots under the control of the truncated replication protein gene promoter, nucleotides 1–184 of SEQ ID NO:1. The truncated promoter can also direct heterogeous gene expression at a high level in other organs of plants, such as leaves and stems. In leaves, the expression level directed by this promoter is 2.4 fold higher than that by the CaMV 35S promoter.

A heterologous gene can also be expressed at a high level under the control of another truncated replication protein gene promoter, nucleotides 1–278 of SEQ ID NO:1. In leaves, the expression level directed by this promoter is 6.6 fold higher than that by the CaMV 35S promoter.

A heterologous gene can further be expressed at a high level under the control of another truncated replication protein gene promoter, nucleotides 1–294 of SEQ ID NO:1. In leaves, the expression level directed by this promoter is 10.9 fold higher than that by the CaMV 35S promoter.

Histochemical assay were performed on root, stems and leaves of plants transformed with a vector containing the GUS gene controlled by each of different truncated promoters. The results showed that positions 141–184 contains essential regulatory elements for specific expression in root. The replication protein gene promoter lost its function to direct expression in root without the element represented by positions 141–184. However, this does not exclude the possibility that the promoter without positions 141–184 may direct expression in other tissues.

The activity of the full length (nucleotides 1–436) replication protein gene promoter is 2 times higher than that of the CaMV 35S promoter in Agrobacterium.

The activity in another direction of the promoter, namely the coat protein gene promoter, is very low, 5 times of background (FIG. 4). However, transient expression of genes directed by this promoter can be increased by activation with the AC2 protein (see table 2 below). AC2 gene can act as a switch for gene expression controlling the initiation and termination of transcription directed by the coat protein gene promoter.

TABLE 2

Comparison between transient expression of GUS gene in cotton and tobacco leaves directed by the CLCuV coat protein gene promoter

| Plant tissues | CP (coat protein) gene promoter-GUS | CP promoter-GUS and CaMV 35S promoter-AC2 | RP promoter-GUS |
|---|---|---|---|
| Cotton leaves | +/− | ++ | +++ |
| Tobacco leaves | +/− | +++ | ++++ |

Notes:
relative value of transient expression directed by the promoters was indicated by the number and intensity of blue spot for each construct of plant expression products which was stained by histochemical method. +/− presents very low activity, ++ presents high activity, +++ presents higher activity, ++++ presents very high activity. CP presents the coat protein gene promoter; RP presents the replication protein gene promoter; CaMV 35S presents the cauliflower mosaic virus 35S promoter; AC2 presents the CLCuV AC2 gene.

BRIEF DESCRIPTION OF THE DRAWINGS

FIG. 1 shows the DNA sequence (SEQ ID NO:1) from CLCuV bi-directional promoter. The upper row number indicates the numbering of nucleotide sequence of the promoter fragment with G as the first nucleotide. The number in the lower row represents the numbering in the original genome. The primers used in PCR are underlined. E presents the shortest promoter sequence (1–149), and B(1–184), C(1–278), D(1–294), A (1–436) presents the promoter with added regulatory elements, respectively. Arrows present the position of nucleotides.

FIG. 2 shows the nucleotide sequence, SEQ ID NO:2, and deduced amino acid sequence, SEQ ID NO:3, of the AC2 protein gene from CLCuV. The AC2 gene was obtained by PCR using total DNA of CLCuV-infected tomato leaves as a template. The full-length PCR product has 521 nucleotides, including a 450 bp encoding region (150 amino acids), two terminator codons (shown by asterisks) and a 52 bp non-coding sequence (shown by lower case letters). Underlined sequences indicate the primer sequences used in PCR. The upper row number indicates the numbering of the nucleotide sequence and the lower row number represents the numbering of the amino acid sequence.

FIG. 3 is a bar drawing showing GUS enzyme activity of stably transformed various tobacco plants with plasmid vector pRPGUS 2300. The exciting wavelength for detecting GUS activity is 365 nm, and the emission wavelength is 455 nm. CLCuV PRP represents the CLCuV replication protein gene promoter-gus transgenic plants; CLCuV PCP represents the CLCuV replication protein gene promoter-gus transgenic plants; CaMV P35S represents the CaMV 35S promoter-gus transgenic plants; CK represents the non-transformed plants as control. GUS activity value is the absolute value without excluding background level. The unit is pmoles MU/mg protein/min.

Figure 4:
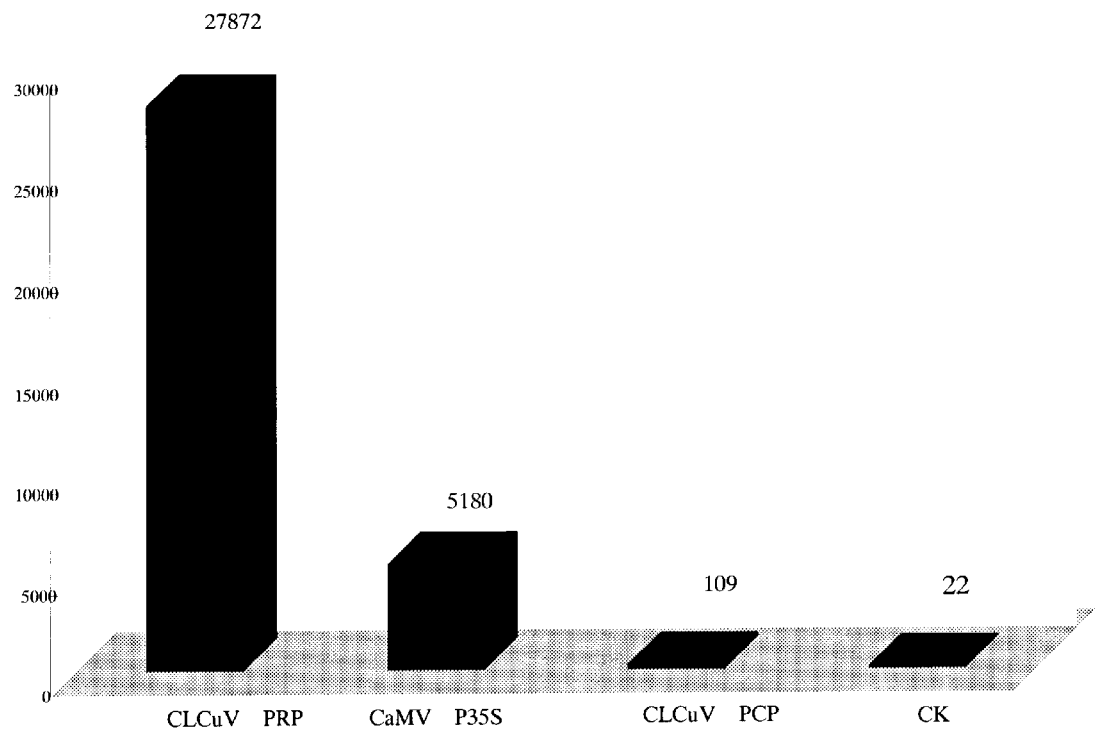

FIG. 4 is a bar drawing which shows GUS enzyme average activity of stably transformed various tobacco plants with the plasmid vector pRPGUS 2300, pCPGUS2300 and pBI121. The exciting wavelength is 365 nm, and the emission wavelength is 455 nm. CLCuV PRP represents the CLCuV replication protein gene promoter-gus transformed plants; CaMV P35S represents the CaMV 35S promoter-gus transformed plants; CK represents the non-transformed plants used as control. GUS activity value indicated above each bar is an absolute average value without excluding the background level. The unit is pmoles MU/mg protein/min.

Figure 5:
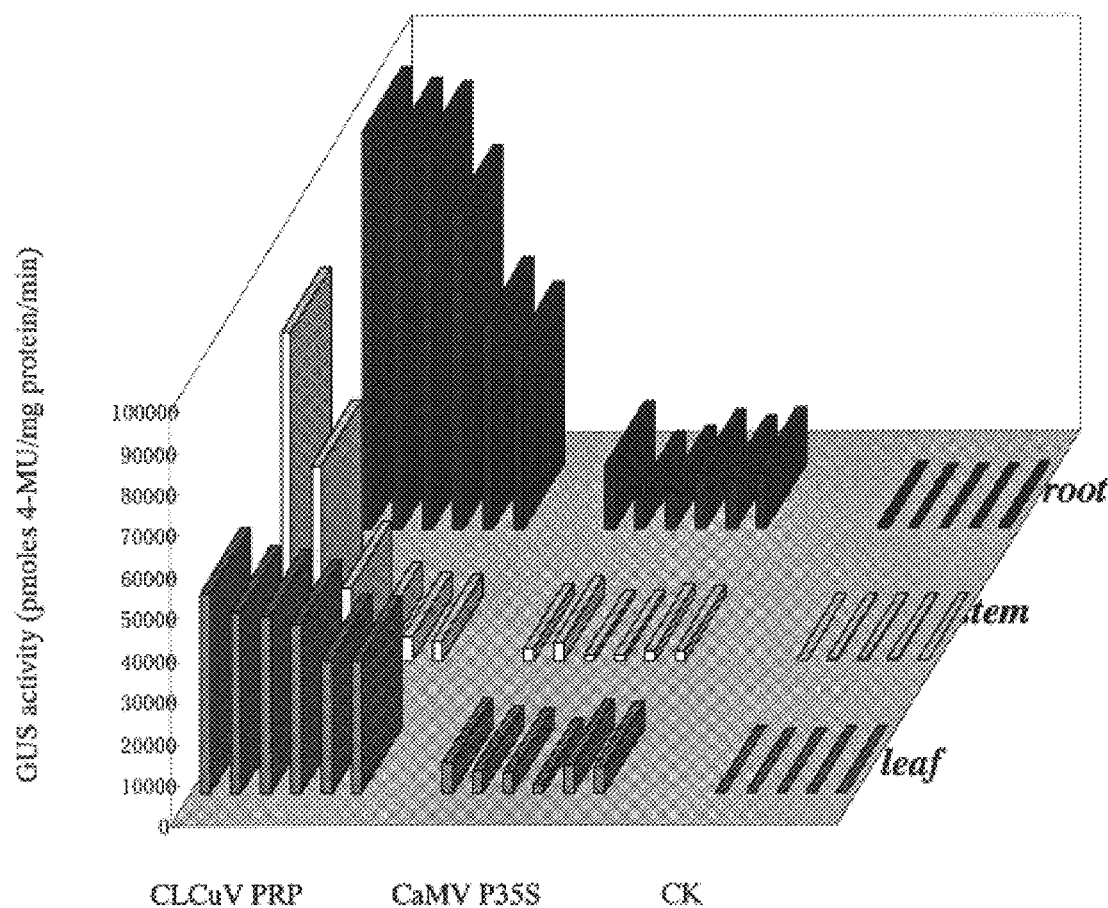

FIG. 5 is a bar drawing which shows GUS enzyme activity of stably transformed various tobacco plants with the plasmid vector pRPGUS 2300 in leaves, stems and roots. The exciting wavelength is 365 nm, and the emission wavelength is 455 nm. CLCuV PRP represents the CLCuV replication protein gene promoter-gus transformed plants; CaMV P35S represents the CaMV 35S promoter-gus transformed plants; CK represents the non-transformed plants used as control. GUS activity value is an absolute value without excluding the background level. The unit is pmoles MU/mg protein/min.

Figure 6:
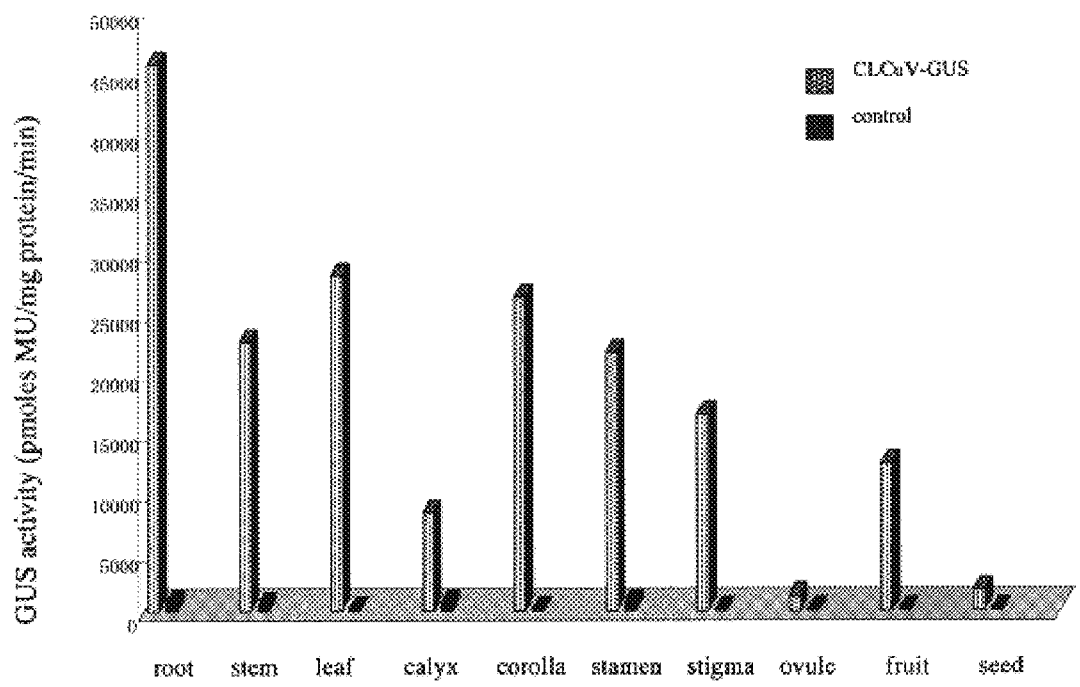

FIG. 6 is a bar drawing which shows GUS enzyme activity of the stably transformed various tobacco plants with the plasmid vector of pRPGUS 2300 in leaves, stems, roots and reproductive organs. The exciting wavelength is 365 nm, and the emission wavelength is 455 nm. CLCuV PRP: CLCuV replication protein gene promoter-gus transformed plants; CaMV P35S CaMV 35S promoter-gus transformed plants; CK: non-transformed plants as control. GUS activity value is an absolute value without excluding the background level. The unit is pmoles MU/mg protein/min.

Figure 7:
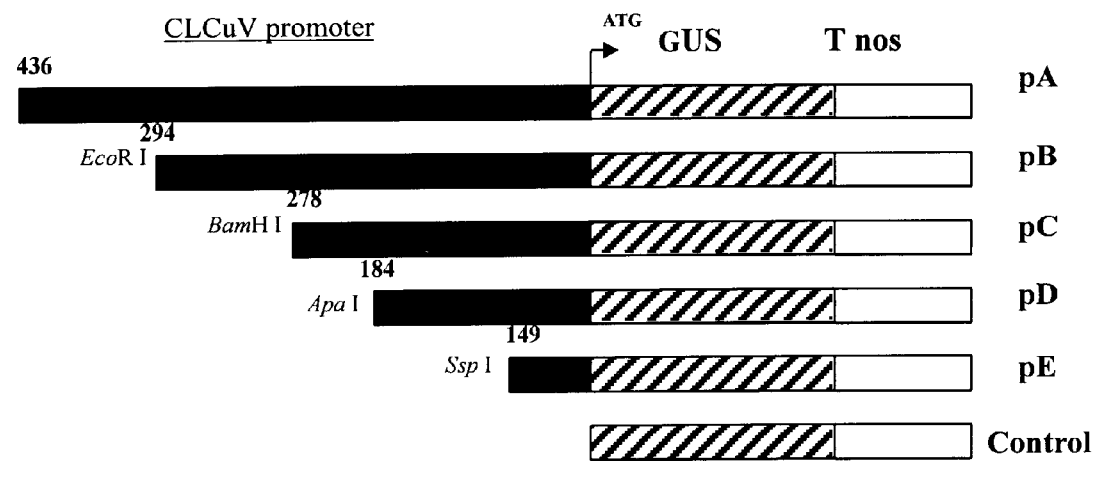

FIG. 7 schematically represents the CLCuV replication protein gene promoter truncated at the 5' end, ligated to the GUS gene and inserted into a plasmid. pA represents full-length promoter construction; pB, pC, pD, pE respectively represents various truncated promoter of 1–294, 1–278, 1–184, and 1–149. CK represents promoter free GUS construct pCAGUS.

Figure 8:
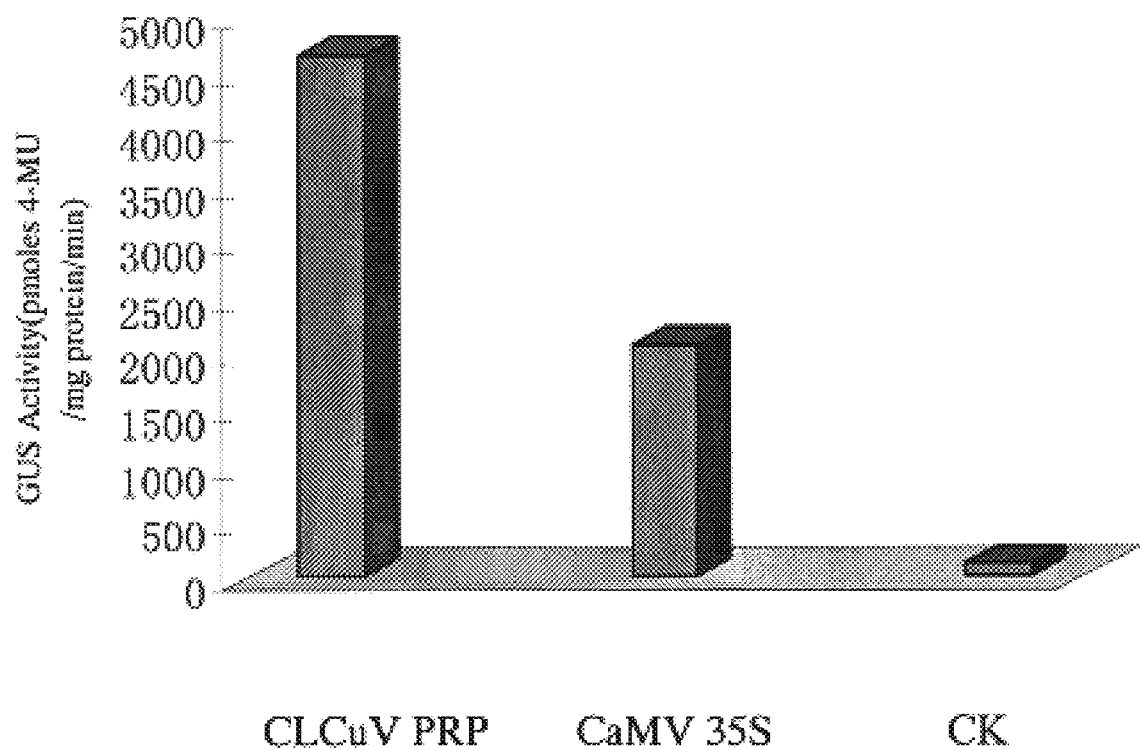

FIG. 8 is a bar drawing which shows GUS enzyme activity in Agrobacterium transformed with a plasmid containing a fusion gene of the CLCuV replication protein gene promoter and GUS gene. The exciting wavelength is 365 nm, and the emission wavelength is 455 nm. CLCuV PRP represents Gus activity of CLCuV replication protein gene promoter-gus transformed plants; CaMV P35S represents the GUS activity of CaMV 35S promoter—gus transformed Agrobacterium; CK represents the non-transformed Agrobacterium used as control. GUS activity value is absolute value without excluding background level. The unit is pmoles MU/mg protein/min.

Figure 9:
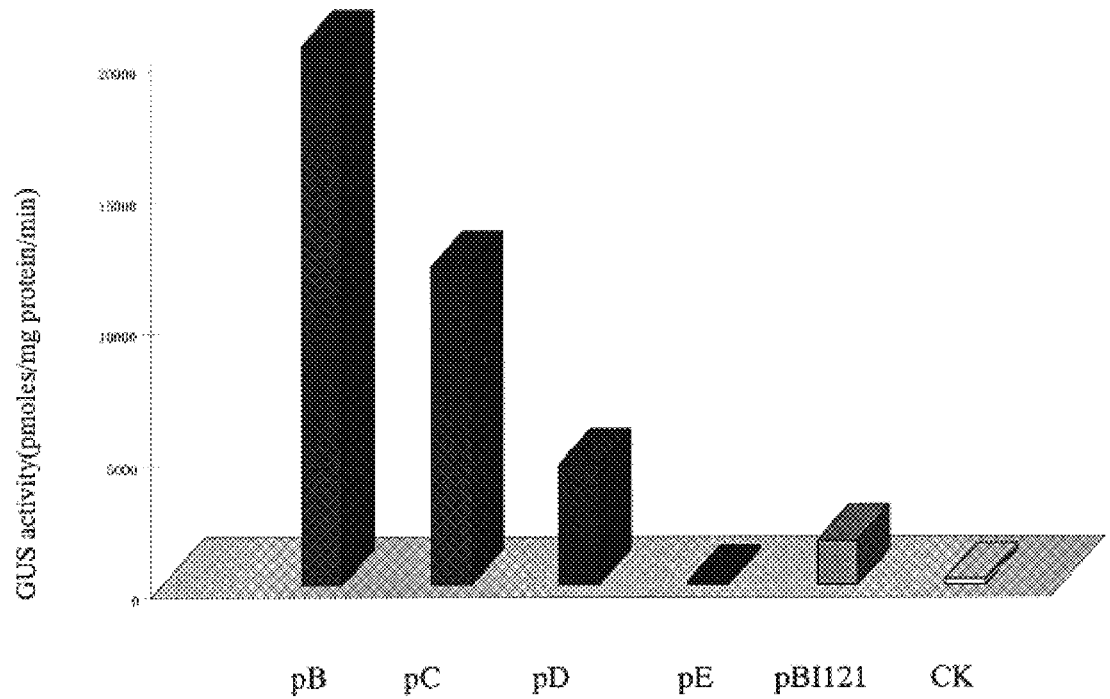

FIG. 9 is a bar drawing which shows GUS enzyme activity in transgenic tobacco leaves transformed with plasmid vector containing a fusion gene of various truncated CLCuV replication protein gene promoter and GUS gene. The exciting wavelength is 365 run, and the emission wavelength is 455 nm. pB, pC, pD, pE respectively represents vectors containing various truncated promoters including 1–294, 1–278, 1–184, and 1–149; pBI121 represents the CaMV 35S promoter vector. CK represents a control containing no promoter-GUS construct, pCAGUS.

EXAMPLES

The efficiency of the promoters to direct expression of heterologous genes was evaluated by measuring GUS activities of transgenic tobacco plants or transient expression in cotton leaves transformed by Agrobacterium containing plasmid of the promoter-gus fusion gene. The following is the methods of vector construction and transformation.

Cloning of Promoter

According to the method of Harrison B. D. et al. (B. D. Harrison et al., 1997, "Detection and Relationships of Cotton Leaf Curl Virus and Allied Whitefly-Transmitted Geminiviruses Occurring in Pakistan", Ann. Appl. Biol., 130: 61–75), the total DNA was extracted from the leaves of CLCuV infected tobacco, and the total DNA was used as a template for PCR. The bi-directional promoter fragment P1P2 was obtained by using the following primers (forward primer: 5-CGGGAGCTCATGATTACGGGAGCGTAAAATAC-3' (SEQ ID NO:6); reverse primer: 5'-CGCGGTACCATGGTGGCAATCGGTGTACACTC-3' (SEQ ID NO:7)). In these two primers, restriction site Kpn I and Sac I were added, respectively. PCR amplified fragment was cut by Kpn I and Sac I and was ligated into the Kpn I/Sac I sites of pGEM7Zf(+)(promega), to obtain a plasmid pGEM7ZP1P2.

Construction of Expression Vector Containing RP Promoter-GUS

Plasmid pAMVGUS contains a NcoI-SalI enzyme digestion fragment containing the GUS gene and Tnos terminator, which is 2.137 kb in length. This fragment was cloned downstream of the P1 promoter (replication protein gene promoter) of pGEM7ZP1P2 at NcoI-XhoI enzyme digestion site, obtaining a plasmid pRPGUS. This plasmid can be used as a transient expression vector. To construct a vector for transforming plants, a SacI-XbaI fragment, containing the structure RP promoter-GUS-nos of pRPGUS with a length of about 2.5 kb, was inserted into pCAMBIA2300 (obtained from CAMBIA) at the same enzyme digestion site. A plasmid pRPGUS2300 suitable for Agrobacterium-mediated transformation was thus obtained. The plant expression vector pBI121 was used as a control and contains the structure, 35S promoter-GUS of CaMV.

Construction of Expression Vector Containing CP Promoter-GUS

Plasmid pDMC203 contains a fragment containing the GUS gene and the nos terminator. The promoter fragment, cut from pGEM7ZP1P2 by Xho I/BspH I, was inserted into pDMC203 at the XhoI-NcoI digestion site to construct pCPGUS. The plasmid can be used as a transient expression vector. To construct a plant expression vector, a fragment containing the CP promoter-GUS-nos digested from pCP-GUS by Bgl II/Xho I with a length of about 2.5 kb was inserted into a plant expression vector, pCAMBIA2300 (obtained from CAMBIA), thereby a plant expression vector pCPGUS2300 suitable for Agrobacterium-mediated transformation was obtained.

Isolation of Trans-acting Factor AC2 and Construction of Expression Vector

The AC2 gene fragment was obtained by PCR using total DNA extracted from CLCuV infected tobacco leaves as the template and the following oligonucleotides as templates (forward primer: 5-CGCGAATTCCTAGACGAGGAAAAGAAGAC-3' (SEQ ID NO:8); reverse primer: 5'-CGGGTCGACTCTATTAATTGAAATTACACCGAG-3' (SEQ ID NO:9)). The 5' end of THE PCR product was digested with EcoR I and the 3' end was blunted by Klenow polymerase and inserted into EcoR I/Sma I sites of cloning vector pBluescriptKS(+). A plasmid pBlueAC2P was obtained. Plasmid pBPF 7 contains a non-translated enhancer sequence of Ω factor, CaMV 35S promoter and nos terminator. pBlueAC2P was digested by EcoR I/Xba I and the fragment containing AC2 expression cassette was then inserted into the EcoR I/Xba I sites of pBPF 7. An expression vector pBPFAC2 was obtained. pBPFAC2 was digested by Hind III and inserted into Hind III site of pCPGUS2300. A combination expression vector of pCPGUS230AC2 was obtained.

Transient Expression and Analysis of Cotton and Tobacco Leaf

The surface fiber was removed from cotton seeds with oil of vitriol. The cotton seeds were washed then with water to remove the vitriol. Afterwards, seed capsules were peeled and the core of the seed were successively soaked in 30% Javelle water for 15 min 0.1% mercury chloride for 4 min and 10% $H_2O_2$ for 20 min sterilization. Tobacco seeds were sterilized by soaking in 30% Javelle water for 10 min. The seeds treated with above methods were germinated under 16 hours photoradoatopm at 25° C. for 30–40 days. Afterwards, the leaves of the asceptic plants were used in transformation. The leaves were spread on hormone free MS basic media, then the plasmids pRPGUS, pCPGUS, and pCPGUS230AC2 were delivered into the leave cells by particle bombardment. The preparation of gold microcarrier and transformation were carried out according to the published method (Ren Yanguo et al., 1998, Transient expression of GUS gene induced by rice psbA promoter in tobacco chloroplast, Journal of Agricultural Biotechnology, 3: 78–83). After 3 days of cultivation in darkness, histochemical staining was carried out on the leaves (R. A. Jeffson, 1987, Assaying chimeric genes in plants: the GUS gene fusion system. Plant Mol. Biol. Rep. 5: 387–405). The leaves were decolored with 70% alcohol to remove the chlorophyll. The result shows that the activity of the coat protein promoter by itself was very low, whereas higher activity was obtained after activation by AC2 factor.

Transformation and Analysis of Tobacco

Plasmids were introduced into Agrobacterium LBA4404 by electroporation. As single colony of Agrobacterium was selected and incubated in 20 ml liquid YEB medium with rifampicin (50 mg/l) and kanamycin (50 mg/l) at 28° C. overnight (150–180 rpm). 400 µl of Agrobacterium incubated in the liquid YEB medium is transferred into 20 ml liquid YEB medium without antibiotics plus 2.5 ml 100 mmol/L Acetosyingone and the incubation was continued for 3–5 hours.

Tobacco leaves were transformed using leaf discs by a known method (R. B. Horsch, 1985, "A Simple Method and General Method for Transferring Genes into Plant", Science, 227: 1229–1230). Leaf discs from sterile plants were infected with Agrobacterium by soaking them in 20 ml of a sterile MS liquid medium containing $10^8$ Agrobacteriuum for 10 min. Afterwards, the explants were bolt dry with sterile filter paper, and incubated on co-cultivation media in darkness for 2 days. Then the leaf discs were transferred to subculture media and cultivated under 16 hours of photoradiation for 3 days. Thereafter, the leaf discs were transferred to selective media and cultivated for 7–10 days and then transferred to regeneration media. The explants were cultivated on regeneration media until the length of the shoots reached 3–4 cm, and then the shoots were cut with a scalpel and transferred to robust media. When the roots had grown out, plants with about the same size were selected to measure their GUS activity. The measurement was conducted by using known methods (R. A. Jeffson, 1987, Assaying chimeric genes in plants: the GUS gene fusion system. Plant Mol. Biol. Rep. 5: 387–405). The results show that the average GUS activity driven by CLCuV RP promoter was 5–6 folds of that of the CaMV 35S promoter.

Histochemical localization (R. A. Jeffson, 1987, "Assaying Chimeric Genes in Plants: the GUS Gene Fusion System", Plant Mol. Biol. Rep. 5: 387–405) was carried out by using unarmed slices or freezing slices. The results showed that the RP promoter function in most of plant organs and tissues except pollen. It is a paraconstitutive promoter.

Transformation of Cotton a Dicotyledonous Plant, Via *Agrobacterium tumefaciens*

The plasmid pRPGUS2300 was introduced into Agrobacterium LBA4404 by electroporation, and was introduced into cotton via the transformed Agrobacterium. Specifically, cotton seeds are put into oil of vitriol to get rid of the surface fiber and washed with water to remove the vitriol. Then the seeds are surface sterilized with 10% $H_2O_2$ for 2–4 hours and washed with sterile water, and finally, the seeds were dipped in water for 12–14 hours. After germination, 5-day old seedlings grown in darkness at 28° C. on ½ MS solid media are used to obtain hypocotyl segments 0.5–1.0 cm in length. Single clone of Agrobacterium is selected and incubated in 20 ml liquid YEB medium with rifampicin (25 mg/l) and kanamycin (50 mg/l ) at 28° C. overnight (150–180 rpm). 400 ul of Agrobacterium incubated in the liquid YEB medium is transferred into 20 ml liquid YEB medium without antibiotics plus 2.5 ml 100 mmol/L acetosyingone and the incubation was continued for 3–5 hours. The transformation was performed by infecting the hypocotyl segments from cotton aseptic seedling for 10 minutes with Agrobacterium which has a concentration of $5 \times 10^8$/ml. After 3-day co-cultivation on co-cultivation medium (MS salts, $B_5$ vitamin, glucose 30,000 mg/L, 2,4-D 0.1 mg/L, KT 0.1 mg/L, Acetosyingone 0.2 mM, pH5.8), kanamycin-resistant (km$^r$) calli were induced and screened on selective medium (MS salts, $B_5$ vitamin, glucose 30,000 mg/L, 2,4-D 0.1 mg/L, KT 0.1 mg/L, Kanamycin 80 mg/L, Cefotaxime 500 mg/L) for 2–3 months (subcultured every 20–30 days). Then the km$^r$ calli were transferred onto inducing medium (MS salts, B$_5$ vitamin, glucose 30,000 mg/L) to induce embryonic calli for about 4–5 months, and the embryonic calli were transferred onto differentiation medium (MS salts without NH$_4$NO$_3$, KNO$_3$ 1,900 mg/L, B$_5$ vitamin, glucose 24,000 mg/L, Glutamin 1,000 mg/L, Aspragine 500 mg/L) to produce somatic embryos. After subcultured every month, transgenic cotton plantlets were obtained and grafted or transplanted when they produced strong root systems.

To graft the regenerated plantlets, shoot apexes of regenerated plantlets with 3–4 leaves were cut down and pared to insert into the top of the stock, which was geminated from untransformed seeds, and grown in greenhouse at 26–28° C. for about 2 weeks until 3–4 leaves were produced. This was performed according to our previously described method.

Monocotyledonous Rice Transformation

1) Construction of plant expression vector:

The plasmid pRPGUS was digested with Sac I/Xba I. The PRP-GUS-Tnos fragment was isolated and inserted into the site Sac I/Xba I of the vector pCAMBIA 1300. A plant expression vector pRPGUSHyg was obtained. The selective marker is hpt (hygromycin) gene.

2) Transformation by particle bombardment

Target tissues used for bombardment were immature embryos or embryogenic calli (embryogenic callus particles isolated from bright yellow, compact embryogenic calli, which is 1 mm in size) derived from immature embryos, which were dissected from surface-sterilized immature seeds approximately 12–15 days after pollination. The target tissue was placed on induction media and was cultured for 2–3 days. The embryos with swelled scutellar side up were transferred onto the osmotic medium (induction medium plus 0.5 M mannitol) in a Petri dish 9 cm in diameter. The embryos were collected at the center of the Petri dish in the range of 2–3 cm for bombardment. The bombarded was performed after 4 hours high osmotic treatment. The embryogenic calli was also subject to osmotic treatment before bombardment. 60 mg of gold particle (1 mm in diameter) was weighed into a 1.5 ml Eppendorf tube. 1 ml of 70% ethanol was added to the tube. The tube was then vortexed and the particle was soaked in the ethanol for 15 min. The particles are then pelleted by centrifugation at 13,000 rpm for 3 minutes. The supernatant is carefully removed and 1 ml of sterile water is added. The tube is once again centrifuged and the supernatant is discarded. The particles were washed for 3 times, and after the final wash, the particles were brought into 1 ml of sterile water. Gold particles can be stored at −20° C. 50 µl gold particles were placed into an Eppendorf tube after vortexed. The following components were then added slowly when the Eppendorf is in vortex: 5 µl DNA (1 µg/µl), 50 µl of 2.5 M CaCl$_2$ (autoclave for sterile), and 20 µl of 0.1 M spermidine. The mixture was then incubated for 10 minutes on a vortex shaker (to fully adhere DNA to microcarriers), then the particles are pelleted by centrifugation at 13,000 for 5 seconds and the supernatant was discarded. The particles were then washed with 250 µl of 100% ethanol, vortexed at 10,000 rpm for 5 sec, and the supernatant was discarded. The particles are resuspended in 60 µl of 100% ethanol and bombarded 5 times (5–10 µl/one bombardment). Biolistics were laid on a cleaner bench. The main chamber was sterilized by spraying with 70% ethanol. The macrocarriers and rupture disks are sterilized by soaking in 70% ethanol for 30 minutes, and were then air dried in a cleaner bench. Macrocarrier holder and stopping screens were sterilized by autoclaving. To load the macrocarriers, 6 µl of coated particles are pipetted onto the center of a macrocarrier, and the loaded macrocarriers were dried. The rupture disk is placed in the recess of the cap, then screwed back into place with a torque wrench. A sterile stopping screen was inserted on the support, a macrocarrier with the microcarriers facing down is then positioned on top of the fixed nest. The cover lid is then replaced and the entire assembly is positioned in the chamber. The procedure for bombardment is performed as follows: (1) turning on the vacuum pump and unit switch and opening the valve to the Helium tank, with the helium regulator set at 1,300 psi; (2) placing the target tissues on the shelf approximately 60–70 mm below the stopping screen shelf; (3) evacuating the chamber (vacuum grade is 27–28 inch mercury); (4) bombarding the tissues; (5) releasing the vacuum in the chamber, removing the sample, and sealing the Petri dish with parafilm. After bombardment, the tissues were placed on the osmotic medium overnight, and then transferred to the induction medium and cultured for 5–7 days. After that, the tissues were transferred to selective medium containing Hyg B 30, 40, and 50 mg/L for japonica, and 20, 30, 40 mg/L for indica. The calli were cultured in dark on the selective medium for three selections, and 3–4 weeks for each selection. The Hyg B resistant calli were transferred onto the differentiation medium with 16 hours of light per day to initiate regeneration, which were previously cultured in the dark for 10 days. When the sprouts reached 2–3 cm, they were transferred into robust medium containing Hyg B 30–50 mg/L (Hyg B 30 mg/L for indica and 50 mg/L for japonica). After the sprouts were produced, they were transferred from the solid medium to a container with a nutrient fluid for opening culture. Well-grown plantlets were transplanted to a greenhouse or a field when young roots have sprouted.

The following is the component of medium.

1. Basic medium (1 L):
    Macronutrient: N$_6$
    Micronutrient: MS
    Fe salt: MS
    Organic-nutrient: B$_5$
    MgCl$_2$: 500 mg
    Glutamine: 250 mg
    L-proline: 500 mg
    Casein enzymatic hydrolysate: 300 mg
    Sucrose: 30,000 mg
    Gelrite: 2,200 mg
2. Induction medium (1 L): Basic medium added 2,4-D: 2 mg.
3. Selective medium (1 L): Basic medium added: 2,4-D: 2 mg
    Hyg B: 30, 40, or 50 mg (for japonica)
        10,20,40 or 50 mg (for indica)
4. Differentiation medium (1 L): Basic medium added
    KT: 2–4 mg
    6-BA: 0.5–1 mg
    NAA: 0.25–0.5 mg
    Hyg B: 30 mg
    Mannitol: 20,000–30,000 mg
5. Robust medium (1 L):
    Macronutrient: ½ MS
    Micronutrient: ½ MS
    Fe salt: ½ MS
    Organic-nutrient: ½ B5
    MgCl2: 500 mg
    Glutamine: 250 mg
    CH: 300 mg Sucrose: 20,000 mg
Gelrite: 2,200 mg Construction of Truncated RP Promoter-GUS Chimeric Gene Expression Vectors pDMC202 (obtained from CAMBIA) is an intermediate plasmid containing the promoterless GUS-Tnos. Firstly, plasmid p7RPGUS202 was constructed by ligating Nco I/Nsi I promoter fragment of pGEM7ZP1P2 into Nco I/Pst I sites of pDMC202. In order to construct plasmids containing truncated promoters having having 5 deletions, p7RPGUS202 was digested by Hind III/Bgl II (including full-length promoter-GUS-Tnos) and inserted into Hind III/BamH I site of the plant expression vector pCAMBIA2300. A plasmid pA was obtained. pB was constructed by digesting p7RPGUS202 with EcoRI, recovering the fragment containing the deleted promoter-GUS-Tnos, and inserting the fragment into EcoR I site of pCaMBIA2300. pC was constructed by digesting p7RPGUS202 with BamH I/EcoR I, recovering the fragment containing the deleted promoter-GUS-Tnos, and inserting the fragment into the same site of pCAMBIA2300. pD was constructed by digesting p7RPGUS202 with Apa I, blunting the product by using Klenow fragment of DNA polymerase I, redigesting p7RPGUS202 with BamHI, recovering a fragment containing the deleted promoter-GUS-Tnos, and inserting the fragment into BamH I/Sma I site of pCAMBIA2300. pE was constructed by digesting p7RPGUS202 with Ssp I/Nco I to obtain a 141 bp promoter fragment, inserting the fragment into the Pvu II/Nco I site pDMC202 to give pSNGUS, digesting pSNGUS with Xho I/Bgl II, recovering a fragment containing the deleted promoter-GUS-Tnos, and inserting the fragment into Sal I/BamH I site of pCAMBIA2300.

pDMC20 was digested with Hind IIII/EcoR I. The fragment GUS-Tnos was recovered and ligated into the Hind IIII/EcoR I site of pBin 19 and pCAMBIA2300, respectively. Plasmids pBinGUS and pCAGUS were obtained and were used as negative control. PBI121 which contains CaMV 35S promoter-GUS-Tnos cassette was used as the positive control.

GUS assay of leaves of PCR positive transgenic plants showed that the truncated promoter 1–149 has the activity to direct heterologous gene expression. The truncated replication protein gene promoter 1–184 showed high activity in roots. This truncated promoter can also direct heterologous gene expression in other tissues such as stems and leaves. The activity in leaves is 2.4 fold of that of CaMV 35S promoter.

A heterologous gene can be expressed at a high level by using the truncated replication protein gene promoter 1–278. In leaves, the expression level directed by this promoter is 6.6 fold of that of CaMV 35S promoter.

A heterologous gene can be expressed at a high level by using the truncated replication protein gene promoter 1–294. In leaves, the expression level directed by this promoter is 10.9 fold of that of CaMV 35S promoter.

Histochemical assays were performed with root, stems and leaves of plants transformed with GUS gene controlled by various truncated promoters. This demonstrated that sequence 141–184 contains essential regulatory elements for expression in root. The replication protein gene promoter without this sequence loses the ability to direct heterologous gene expression in root. However, it does not exclude the possibility for this promoter to direct heterologous gene expression in other organs or tissues. It was further demonstrated that the full-length promoter and 1–184 truncated promoter showed high activity in the meristem of the root tip and the vascular bundle of the root.

Histochemical staining of leaf sections indicated that the full length replication protein gene promoter and the 1–149 truncated promoter showed high activity in mesophyll (including palisade and spongy mesophyll tissues) and vascular tissues, however the intensity of staining was different.

Staining of the stem sections suggested that the full-length and 1~278 truncated promoter showed activity in both external and internal phloem cells and the parenchyma cells of xylem and cortex. However, the 1–184 truncated promoter showed activity only in vascular bundles and no activity in parenchyma cells. The result suggested that cis-element between 149–184 might have phloem specific regulator function.

PCR Analysis of Transgenic Tobacco Plants

Tobacco transformation and screening of regenerated plants were performed according to the known method (R. B. Horsch, 1985, "A Simple Method and General Method for Transferring Genes Into Plant", Science, 227: 1229–1230). 100 mg leaves from kanamycin resistant transgenic plants were taken and total DNA was extracted from it by using the method of B. D. Harrison et al. (B. D. Harrison et al. 1997, "Detection and Relationships of Cotton Leaf Curl Virus and Allied Whitefly-Transmitted Geminiviruses Occurring in Pakistan", Ann. Appl. Biol., 130: 61–75). The total DNA was dissolved in 50 $\mu$l TE buffer. The GUS gene fragment was amplified by PCR by using the method of B. D. Harrison et al. (B. D. Harrison et al. 1997, Detection and relationships of cotton leaf curl virus and allied whitefly-transmitted geminiviruses occurring in Pakistan. Ann. Appl. Biol., 130: 61~75). The primer sequences are: 5' primer 5'-CTGCGACGCTCACACCGATACC-3' (SEQ ID NO:10); 3' primer 5'-TCACCGAAGTTCATGCCAGTCCAG-3' (SEQ ID NO:11). The result of the PCR amplification showed that GUS gene was integrated into the genome of transgenic plants.

Construction of Expression Vectors, Containing Full-length RP Promoter-GUS Fusion Genes and Transient Expression of Fusion Genes in Agrobacterium pDMC202(obtained from CAMBIA) was an intermediate plasmid vector containing promoterless GUS-Tnos cassette. Firstly, the plasmid pGEM7ZP1P2 was digested by Nco I/Nsi I, the fragment obtained was inserted at the Nco I/Pst I site of pDMC202. A plasmid p7RPGUS202 was constructed. Then the fragment containing full-length promoter-GUS-Tnos cassette digested by Hind III/Bgl II was inserted into Hind III/BamH I site of plant expression vector pBin19 and pBinRPGUS was obtained. pDMC202 was digested with EcoR I/Hind III, a fragment containing GUS-Tnos was recovered, and the fragment was ligated into EcoR I/Hind III site of pBin19, pCAMBIA2300 (obtained from CAMBIA), respectively, and recombinant plasmid pBinGUS, pCAGUS was constructed, which was used as negative control. Positive control was pBI121 containing the CaMV 35S promoter-GUS-Tnos cassette. Each of the above *E. coli* plasmid was introduced into *Agrobacterium tumefaciens* by electroporation. Single colonies were selected and were cultured with shaking for 16 hours at 28° C., then total protein was extracted. Protein extraction and quantitative measurement were carried out according to the method of Jefferson.

Plant expression vector of pBinRPGUS containing full-length promoter-GUS fusion genes was delivered into *Agrobacterium tumefaciens*. The 35S promoter was used as control and GUS activity of total protein in *Agrobacterium tumefaciens* was measured. The result showed that replication protein gene promoter activity was 2-fold of that of the CaMV 35 promoter, 45-fold higher than background of *Agrobacterium tumefaciens*. There is no doubt it is a strong promoter.

GUS Activity Analysis of the Virus Truncated CLCuV Replication Protein Gene Promoter pBinGUS, pCAGUS containing promoterless—GUS was used as negative control and pBI121 containing 35S promoter-GUS-Tnos cassette was used as positive control. The recombinant plasmids pA, pB, pC, pD, pE containing different truncated CLCuV replication protein gene promoter were transferred into *Agrobacterium tumefaciens* by electroporation according to the protocol of BIO-RAD. Promoter activity in *Agrobacterium tumefaciens* was analyzed. The result showed that activity of the five truncated promoters were different from each other. 1–278, 1–294 promoter showed higher activity, and 1–294 promoter activity was 4-fold of that of full-length promoter. But GUS activity directed by 1~184, 1~149 promoters are similar to background.

What is claimed is:

1. An isolated bi-directional promoter, comprised of the CLCuV coat protein gene promoter in one direction and the CLCuV replication protein gene promoter in the other direction, said bi-directional promoter having the nucleotide sequence of SEQ ID NO: 1.

2. A method for expression of one or more heterologous genes in plant tissues by using a bi-directional promoter, comprising the steps of,
   (a) constructing a plant expression vector comprising the bi-directional promoter of claim 1, wherein a heterologous gene is operably linked to the CLCuV coat protein gene promoter and/or the CLCuV replication protein gene promoter,
   (b) introducing the constructed plant expression vector into plant cells, and
   (c) regenerating the transformed plant cells under appropriate conditions to a plant, thereby obtaining transformed plants comprising tissues expressing heterologous genes.

3. The method according to claim 2, wherein one of said heterologous genes is operably linked to the replication protein gene promoter.

4. The method according to claim 2, wherein one of said heterologous genes is operably linked to the coat protein gene promoter and wherein the expression vector further comprises an expression cassette comprising a gene encoding the CLCuV AC2 protein.

5. An isolated promoter consisting of a fragment of the nucleotide sequence of SEQ ID NO: 1, wherein said fragment comprises at least bases 1–149 of SEQ ID NO: 1.

6. The promoter according to claim 5 wherein the fragment consists of bases 1–184 of SEQ ID NO: 1.

7. The promoter according to claim 5 wherein the fragment consists of bases 1–278 of SEQ ID NO: 1.

8. The promoter according to claim 5 wherein the fragment consists of bases 1–294 of SEQ ID NO: 1.

9. A method for expression of a heterologous gene in plant tissues comprising the steps of:
   (a) constructing a plant expression vector comprising the promoter of claim operably linked to a heterologous gene;
   (b) introducing the constructed plant expression vector into plant cells, and
   (c) regenerating the transformed plant cell under appropriate conditions to a plant, thereby obtaining transformed plants comprising tissues expressing said heterologous gene.

* * * * *

SEQUENCE LISTING

<160> NUMBER OF SEQ ID NOS: 11

<210> SEQ ID NO 1
<211> LENGTH: 436
<212> TYPE: DNA
<213> ORGANISM: cotton leaf curl virus

<400> SEQUENCE: 1

```
ggtaccatgg tggcaatcgg tgtacactct aattctctgg caatcggtgt aacggggtgc      60
aatatatagg tgtaccccaa atggcattat cgtaatttga gaaatcattt caaaatcctc     120
acgctccaaa aagcggccat ccgtataata ttaccggatg gccgcgcttt tttttttgtg     180
ggcccccgat ttacgagatt gctccctcaa agctaaataa cgctcccgca cactataagt     240
acttgcgcac taagtttcaa attcaaacat gtgggatcca ctattaaacg aattccctga     300
tacggttcac gggtttcggt gtatgctttc tgtgaaatat ttgcaacttt tgtcgcagga     360
ttattcaccg gatacgcttg ggtacgagtt aatacgggat ttaatttgta ttttacgctc     420
ccgtaatcat gagctc                                                     436
```

<210> SEQ ID NO 2
<211> LENGTH: 517
<212> TYPE: DNA
<213> ORGANISM: cotton leaf curl virus

<400> SEQUENCE: 2

```
cgcaattcct agacgaggaa aagaacaccg cactaaagaa ctgggcagta aagaatgcga      60
tcttcatcac actggataga cccctgtact caggtaccaa tcaaagtaca gcacagggaa     120
gcgaagagcc gcaacaggag gaggagagta gatcttgaat gcgggtgttc ttattatctg     180
tcaatcaact gccacaacca tggattcacg cacagggggaa cccatcactg cagctcaagc     240
agggaatggc gcatatatct gggaggttcc aaatcccctt tatttcaaga tcatcagcca     300
cgtcaaccgt ccattcacga cgaatatgga catactcacg atcaggatcc agttcaacta     360
caacactcgg aaagctctgg gactgcacac gtgttttcta accttccgaa tctggacctt     420
acagcctcag actggtcttt tcttaagggt attcaaaacc caagtcctca aatatctgaa     480
caatctcggt gtaatttcaa ttaatagagt cgaccgg                              517
```

<210> SEQ ID NO 3
<211> LENGTH: 150
<212> TYPE: PRT
<213> ORGANISM: cotton leaf curl virus

<400> SEQUENCE: 3

```
Met Arg Ser Ser Ser His Leu Ile Asp Pro Cys Thr Gln Val Pro Ile
1               5                   10                  15
```

```
Lys Val Gln His Arg Glu Ala Lys Arg Arg Asn Arg Arg Arg Val
             20                  25                  30

Asp Leu Glu Cys Gly Cys Ser Tyr Tyr Leu Ser Ile Asn Cys His Asn
         35                  40                  45

His Gly Phe Thr His Arg Gly Thr His His Cys Ser Ser Ser Arg Glu
 50                  55                  60

Trp Arg Ile Tyr Leu Gly Gly Ser Lys Ser Pro Leu Phe Gln Asp His
 65                  70                  75                  80

Gln Pro Arg Gln Pro Ser Ile His Asp Glu Tyr Gly His Thr His Asp
                 85                  90                  95

Gln Asp Pro Val Gln Leu Gln His Ser Glu Ser Ser Gly Thr Ala His
             100                 105                 110

Val Phe Ser Asn Leu Pro Asn Leu Asp Asp Leu Thr Ala Ser Asp Trp
         115                 120                 125

Ser Phe Leu Lys Gly Ile Gln Asn Pro Ser Pro Gln Ile Ser Glu Gln
     130                 135                 140

Ser Arg Cys Asn Phe Asn
145                 150

<210> SEQ ID NO 4
<211> LENGTH: 6
<212> TYPE: DNA
<213> ORGANISM: Cotton leaf curl virus
<220> FEATURE:
<221> NAME/KEY: misc_feature
<222> LOCATION: (1)..(3)
<223> OTHER INFORMATION: y=pyrimadine
<220> FEATURE:
<221> NAME/KEY: misc_feature
<222> LOCATION: (5)..(5)
<223> OTHER INFORMATION: y=pyrimadine

<400> SEQUENCE: 4 yyyaya                                                                6

<210> SEQ ID NO 5
<211> LENGTH: 57
<212> TYPE: DNA
<213> ORGANISM: Cotton leaf curl virus

<400> SEQUENCE: 5
gctccaaaaa gcggccatcc gtataatatt accggatgcc gcgcttttt ttttgtg       57

<210> SEQ ID NO 6
<211> LENGTH: 32
<212> TYPE: DNA
<213> ORGANISM: Cotton leaf curl virus

<400> SEQUENCE: 6
cgggagctca tgattacggg agcgtaaaat ac                                 32

<210> SEQ ID NO 7
<211> LENGTH: 32
<212> TYPE: DNA
<213> ORGANISM: Cotton leaf curl virus

<400> SEQUENCE: 7
cgcggtacca tggtggcaat cggtgtacac tc                                 32

<210> SEQ ID NO 8
<211> LENGTH: 29
<212> TYPE: DNA
```

```
<213> ORGANISM: Cotton leaf curl virus

<400> SEQUENCE: 8
cgcgaattcc tagacgagga aaagaagac                                29

<210> SEQ ID NO 9
<211> LENGTH: 33
<212> TYPE: DNA
<213> ORGANISM: Cotton leaf curl virus

<400> SEQUENCE: 9
cgggtcgact ctattaattg aaattacacc gag                           33

<210> SEQ ID NO 10
<211> LENGTH: 22
<212> TYPE: DNA
<213> ORGANISM: Cotton leaf curl virus

<400> SEQUENCE: 10
ctgcgacgct cacaccgata cc                                       22

<210> SEQ ID NO 11
<211> LENGTH: 24
<212> TYPE: DNA
<213> ORGANISM: Cotton leaf curl virus

<400> SEQUENCE: 11
tcaccgaagt tcatgccagt ccag                                     24
```